(12) United States Patent
Coupé et al.

(10) Patent No.: US 10,213,434 B2
(45) Date of Patent: Feb. 26, 2019

(54) USE OF FACTOR XA INHIBITORS FOR REGULATING GLYCEMIA

(71) Applicant: VAIOMER, Labege (FR)

(72) Inventors: Bérengère Coupé, Toulouse (FR); Michael Courtney, Lyons (FR)

(73) Assignee: VAIOMER, Labege (FR)

( * ) Notice: Subject to any disclaimer, the term of this patent is extended or adjusted under 35 U.S.C. 154(b) by 0 days.

(21) Appl. No.: 15/565,317

(22) PCT Filed: Apr. 8, 2016

(86) PCT No.: PCT/EP2016/057729
§ 371 (c)(1),
(2) Date: Oct. 9, 2017

(87) PCT Pub. No.: WO2016/162472
PCT Pub. Date: Oct. 13, 2016

(65) Prior Publication Data
US 2018/0161334 A1    Jun. 14, 2018

(30) Foreign Application Priority Data
Apr. 8, 2015 (EP) .................................... 15305518

(51) Int. Cl.
| | | |
|---|---|---|
| *A61K 31/5377* | (2006.01) | |
| *A61K 45/06* | (2006.01) | |
| *A61K 31/7024* | (2006.01) | |
| *A61K 31/4425* | (2006.01) | |
| *A61P 3/10* | (2006.01) | |

(52) U.S. Cl.
CPC ...... *A61K 31/5377* (2013.01); *A61K 31/4425* (2013.01); *A61K 31/7024* (2013.01); *A61K 45/06* (2013.01); *A61P 3/10* (2018.01)

(58) Field of Classification Search
None
See application file for complete search history.

(56) References Cited

U.S. PATENT DOCUMENTS

| 2011/0236474 A1 | 9/2011 | Leonard et al. |
| 2017/0274089 A1 | 9/2017 | Mendelsohn et al. |

OTHER PUBLICATIONS

International Search Report for PCT/EP2016/057729, dated Jun. 29, 2016.
European Search Report for EP 15305518, dated Sep. 9, 2015.
Bauer, Kenneth. (2013). Pros and cons of new oral anticoagulants. Hematology / the Education Program of the American Society of Hematology. American Society of Hematology. Education Program. 2013. 464-70. 10.1182/asheducation-2013.1.464.
Tyan F. Thomas et al: "Rivaroxaban: An Oral Factor Xa Inhibitor", Clinical Therapeutics, vol. 35, No. 1, Jan. 1, 2013 (Jan. 1, 2013), pp. 4-27, XP055211870, ISSN: 0149-2918, DOI: 10.1016/j.clinthera.2012.12.005 the whole document.
Mychka V B et al: "Effect of of enoxaparin on brain perfusion, glucose and lipids metabolism in patients with arterial hypertension and type 2 diabetes mellitus", European Heart Journal, vol. 26, No. Suppl. 1, Sep. 2005 (Sep. 2005), p. 482, XP009185977, & 27th Congress of the European-Society-of-Cardiology; Stockholm, Sweden; Sep. 3-7, 2005 ISSN: 0195-668X the whole document.
Intensive Blood Glucose Control and Vascular Outcomes in Patients with Type 2 Diabetes, Journal of Vascular Surgery , vol. 48 , Issue 3 , 770, pp. 2560-2570, (2008).
Iba, Toshiaki, et al. "Rivaroxaban Attenuates Leukocyte Adhesion in the Microvasculature and Thrombus Formation in an Experimental Mouse Model of Type 2 Diabetes Mellitus." Thrombosis Research, Pergamon, Nov. 25, 2013, www.sciencedirect.com/science/article/pii/S0049384813005495.
Hirayama, Fukushi, et al. "Design, Synthesis and Biological Activity of YM-60828 Derivatives: Potent and Orally-Bioavailable Factor Xa Inhibitors Based on Naphthoanilide and Naphthalensulfonanilide Templates." Bioorganic & Medicinal Chemistry, Pergamon, Apr. 12, 2002, www.sciencedirect.com/science/article/pii/S0968089602001062.
Burcelin, Rémy, et al. "Heterogeneous metabolic adaptation of C57BL/6J mice to high-fat diet." American Journal of Physiology—Endocrinology and Metabolism Published Apr. 1, 2002 vol. 282 No. 4, E834-E842 DOI:10.1152/ajpendo.00332.2001.
Venkateswarlu, Divi, et al. "Structure and Dynamics of Zymogen Human Blood Coagulation Factor x." Biophysical Journal, vol. 82, Dec. 12, 2001, pp. 1190-1206.

*Primary Examiner* — Brian J Davis
(74) *Attorney, Agent, or Firm* — B. Aaron Schulman, Esq.; Stites & Harbison, PLLC

(57) ABSTRACT

The present invention concerns a factor Xa inhibitor for use as a medicament in a method for regulating glycemia in a subject, in particular for use for preventing and/or treating hyperglycemia, impaired glucose tolerance, impaired fasting glucose, insulin resistance and/or diabetes.

10 Claims, 4 Drawing Sheets

USE OF FACTOR XA INHIBITORS FOR REGULATING GLYCEMIA

The present invention concerns methods for regulating glycemia in particular for treating diabetes such as type 2 diabetes.

Over the last decades, the incidence of type 2 diabetes has risen dramatically and this unabated increase can be justly described as a world-wide epidemic.

The current antidiabetic therapies are effective in controlling blood sugar levels but do not show any effect on the cardiovascular complications of diabetes, in particular on the risk of heart attack or heart failure (Advance Collaborative Group (2008) *N. Engl. J. Med.* 358:2560-2572). However, the major cause of death and complications in patients with type 2 diabetes is cardiovascular disease.

There is thus an important need of new antidiabetic therapies enabling both controlling blood sugar levels and preventing cardiovascular complications of diabetes.

Several factor Xa inhibitors are currently used because of their anticoagulant properties for stroke prevention in atrial fibrillation, for treatment and secondary prevention of venous thromboembolism, or for initial treatment and prevention of venous thromboembolism in patients undergoing hip or knee replacement (Bauer (2013) *Hematology* 2013 (1):464-470). It was further shown that rivaroxaban, a factor Xa inhibitor, displayed antithrombotic effects when administered into a mouse model of diabetes (Iba et al. (2014) *Thromb. Res.* 133:276-280).

The present invention arises from the unexpected finding by the inventors that the glycemia of mice rendered type 2 diabetic by feeding with a high fat diet (HFD) can be regulated by oral or subcutaneous administration of rivaroxaban. More particularly, the inventors demonstrated that blood glucose concentration of HFD mice administered with rivoraxaban was reduced compared to untreated HFD mice. Furthermore, the increase of glucose intolerance index induced by the high fat diet in these mice was also reduced when rivaroxaban was administered.

The present invention thus concerns a factor Xa inhibitor for use as a medicament in a method for regulating glycemia in a subject, in particular for use for preventing and/or treating hyperglycemia, impaired glucose tolerance, impaired fasting glucose, insulin resistance and/or diabetes.

DETAILED DESCRIPTION OF THE INVENTION

Factor Xa Inhibitor

In the context of the invention, "Factor Xa", "FXa" or "F10a" refers to a serine protease in the blood coagulation pathway, which is produced from the inactive Factor X (FX or F10). Factor X is activated into Factor Xa by either factor IXa with its cofactor, factor VIIIa, in a complex known as intrinsic Xase, or factor VIIa with its cofactor, tissue factor, in a complex known as extrinsic Xase. Factor Xa forms a membrane-bound prothrombinase complex with factor Va and is the active component in the prothrombinase complex that catalyzes the conversion of prothrombin to thrombin. FXa as well as thrombin also stimulate cell migration and induce the expression of angiogenic factors such as VEGF and bFGF.

The nucleotide sequence encoding human Factor X is referenced under GenBank number NM_000504. The corresponding amino acid sequence and domain structure of Factor X are described in Leytus et al. (1986) *Biochemistry* 25:5098-5102. The domain structure of mature Factor X is also described in Venkateswarlu et al. (2002) *Biophysical Journal* 82:1190-1206. Upon catalytic cleavage of the first 52 residues of the heavy chain, Factor X is activated to Factor Xa. Factor Xa contains a light chain and a heavy chain. The first 45 amino acid residues of the light chain are called the Gla domain because it contains 11 post-translationally modified γ-carboxyglutamic acid residues (Gla). It also contains a short (6 amino acid residues) aromatic stack sequence. Chymotrypsin digestion selectively removes the 1-44 residues resulting in Gla-domainless Factor Xa. The serine protease catalytic domain of Factor Xa locates at the C-terminal heavy chain. The heavy chain of Factor Xa is highly homologous to other serine proteases such as thrombin, trypsin, and activated protein C.

In the context of the invention, the above cited GenBank references are those that were available on Feb. 18, 2015.

As used herein, a "factor Xa inhibitor" is a compound which can inhibit the expression of factor Xa and/or which can inhibit, directly or indirectly the Factor Xa activity, in particular its activity of catalyzing conversion of prothrombin to thrombin in vitro and/or in vivo. The factor Xa inhibitor used in the context of the invention can thus be an inhibitor of factor Xa expression and/or activity.

In a particular embodiment, the factor Xa inhibitor used in the context of the invention is an inhibitor of factor Xa activity. Preferably, the factor Xa activity inhibitor used in the context of the invention is a direct inhibitor of factor Xa activity. A direct inhibitor of factor Xa activity as described herein is an agent capable of directly binding to factor Xa and inhibiting or preventing conversion of prothrombin to thrombin. In another embodiment, the factor Xa activity inhibitor used in the context of the invention is an indirect inhibitor of factor Xa activity. Indirect inhibitors of factor Xa activity as described herein includes agents which inhibit the conversion of factor X into factor Xa or that otherwise inhibit factor Xa without directly binding to factor Xa, for example through antithrombin activation.

Examples of direct inhibitors of factor Xa activity are well-known from the skilled person and include rivaroxaban (CAS n° 366789-02-8), apixaban (CAS n° 503612-47-3), betrixaban (CAS n° 330942-05-7), edoxaban (also called DU-176b, CAS n° 480449-70-5), otamixaban (CAS n° 193153-04-7), DX 9065a (CAS n° 155204-81-2), razaxaban (CAS n° 218298-21-6), darexaban (also called YM-150, CAS n° 365462-23-3), letaxaban (CAS n° 870262-90-1), LY517717 (CAS n° 313489-71-3), YM-60828 (CAS n° 179755-65-8), eribaxaban (CAS n° 536748-46-6), JTV-803 (CAS n° 247131-79-9), DPC-423 (CAS n° 292135-59-2), RPR-209685 (CAS n° 234100-28-8), BMS-740808 (CAS n° 280118-23-2), antistasin, NAP-5 protein, YM466 of the following formula (I)

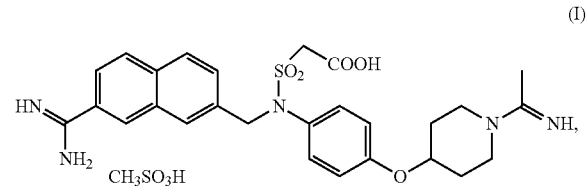

GW813893 of the following formula (II)

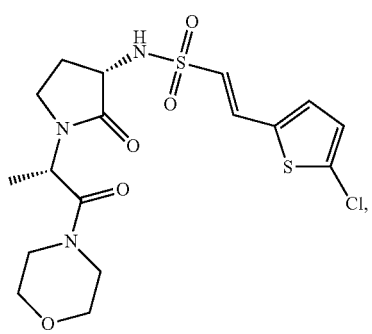

KFA-1411 of the following formula (III)

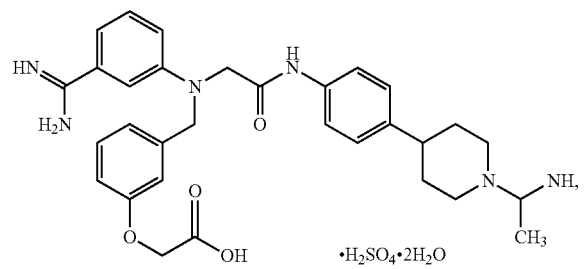

MCM-09 of the following formula (IV)

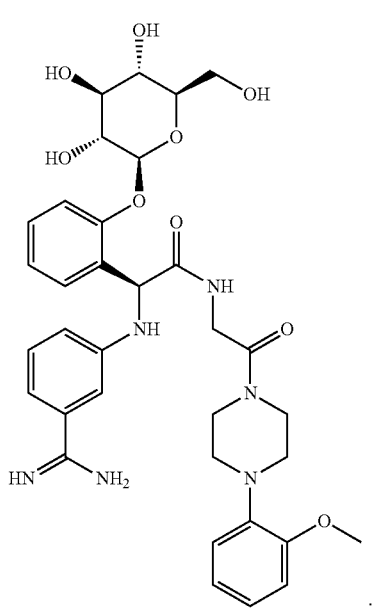

Other examples of direct inhibitors of factor Xa activity include the compounds defined in the patent applications WO 02/16312, WO 2006/083003, WO 2007/031343, WO 2006/008141, US 2008051688, WO 2006/047415, DE 102007037373, WO 2009/018807, US 2006040973, US 2007135426, DE 102005018690, WO 2007/051532, WO 2007/039134, DE 102005048824, DE 102005045518, WO 2008/052671, WO 2008/155034, WO 2007/137792, DE 102006025316, WO 2007137800, WO 2007/137793, WO 2007/137801, WO 2006/061116, WO 2006/058630, WO 2007/028520, WO 2007/003536, WO 2007/009963, US 2006142263, WO 2008/116881, WO 2007/025940, WO 2007/131982, WO 2008/135524, EP 1818330, DE 102004060984, WO 2008/135526, DE 102004047840, WO 2008/135525, WO 2006/048152, WO 2007/122104, EP 1846381, US 2007015812, US 2007135426, US 2008090807, WO 2006/041831, US 2006089496, WO 2006/002099, US 2007259924, WO 2008/086226, WO 2008/057972, WO 2007/059952, US 2007155745, EP 1839659, WO 2006/106963, WO2008/111299, WO 2008/111300, WO 2008/123017, WO 2007/008144, WO 2007/008145, WO 2007/008142, WO 2007/008146, WO 2006/057845, WO 2006/057868, JP 2007045752, WO 2006/063113, WO 2006/063293, WO 2008/065503, WO 2006/122661 and WO 2008/140220.

Preferably, the direct inhibitor of factor Xa activity used in the context of the invention is selected from the group consisting of rivaroxaban, otamixaban, darexaban, LY517717 and eribaxaban.

Examples of indirect inhibitors of factor Xa activity are well-known from the skilled person and include fondaparinux (CAS n° 114870-03-0), idraparinux (CAS n° 162610-17-5), biotinylated idraparinux (also called idrabiotaparinux, CAS n° 774531-07-6), enoxaparin, dalteparin sodium (also called fragmin), low molecular weight heparin (LMWH), bemiparin, nadroparin, reviparin, parnaparin, certoparin, tinzaparin, rNAPc2 and tissue factor pathway inhibitor.

Preferably, the indirect inhibitor of factor Xa activity used in the context of the invention is selected from the group consisting of fondaparinux, idraparinux, idrabiotaparinux and enoxaparin.

Techniques to identify inhibitors of factor Xa activity are well-known from the skilled person and are for example described in Hirayama et al. (2002) Bioorg. Med. Chem. 10:2597-2610. A conventional test is the chromogenic anti-factor Xa assay. Typically, the technique to identify inhibitors of factor Xa activity may be carried out as followed. The hydrolysis rates of a synthetic chromogenic factor Xa substrate, such as the BioPhen CS-11(22) compound (commercialized by Hyphen BioMed) or the S-2222 compound (commercialized by Chromogenix), are assayed by continuously measuring absorbance at 405 nm at 37° C. Reaction mixtures are prepared containing the chromogenic substrate Xa and the candidate inhibitor in 0.05 M Tris HCl, pH 8.4, 0.15 M NaCl. Reactions are initiated with a Factor Xa solution. The concentration of the candidate inhibitor required to inhibit factor Xa activity by 50% ($IC_{50}$) may then be calculated from dose-response curves in which the logit transformation of residual activity is plotted against the logarithm of candidate inhibitor concentration.

Preferably, the inhibitor of factor Xa activity used in the context of the invention is selected from the group consisting of rivaroxaban, otamixaban, darexaban, LY517717, eribaxaban, fondaparinux, idraparinux, idrabiotaparinux, enoxaparin, factor Xa blocking antibodies or antibody fragments and aptamers.

In particular, the inhibitor of factor Xa activity may consist in an antibody directed against factor Xa, in such a way that said antibody impairs the binding of factor Xa to its target. Examples of anti-factor Xa antibodies are well-known from the skilled person and include the anti-Factor Xa rabbit polyclonal antibody ab111171 commercialized by Abcam, the human coagulation Factor X/Xa monoclonal antibody (Clone 156106) commercialized by R&D Systems and the anti-human Factor X/Xa calcium dependent antibody (Clone CaFX-50) commercialized by MyBioSource.

Antibodies directed against factor Xa can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against factor Xa can be prepared and isolated using any technique that provides for the production of antibody molecules by continuous cell lines in culture. Techniques for production and isolation include the hybridoma technique originally described by Kohler and Milstein (1975) Nature 256:495-497; the human B-cell hybridoma technique (Cote et al. (1983) Proc Natl Acad Sci U S A. 80:2026-2030); and the EBV-hybridoma technique (Cole et al. (1985) Monoclonal Antibodies and Cancer Therapy, Alan R. Liss, Inc., pp. 77-96). Alternatively, techniques described for the production of single chain antibodies (see, e.g., U.S. Pat. No. 4,946,778) can be adapted to produce anti-factor Xa single chain antibodies. Inhibitors of factor Xa activity useful in practicing the present invention also include anti-factor Xa antibody fragments including F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to factor Xa.

Humanized anti-factor Xa antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, use may be made of aptamers.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk and Gold (1990) Science. 249:505-510. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena (1999) Clin Chem. 45:1628-1650. Peptide aptamers consist of a conformationally constrained antibody variable region displayed by a platform protein, such as E. coli Thioredoxin A that are selected from combinatorial libraries by two hybrid methods (Colas et al. (1996) Nature 380:548-550).

Preferably, the inhibitor of factor Xa activity used in the context of the invention is selected from the group consisting of rivaroxaban, otamixaban, darexaban, eribaxaban, fondaparinux, idraparinux, idrabiotaparinux, enoxaparin and factor Xa blocking antibodies or antibody fragments.

Still preferably, the inhibitor of factor Xa activity used in the context of the invention is selected from the group consisting of rivaroxaban, otamixaban and idraparinux.

Still preferably, the inihibitor of factor Xa activity used in the context of the invention has a low oral bioavailability.

By "oral bioavailability" is meant herein the fraction of an orally administered dose of unchanged drug that reaches the systemic circulation. Bioavailability is typically assessed by determining the area under the plasma concentration-time curve (AUC). Since drugs administered intravenously have 100% bioavailability, the level of oral bioavailability is typically the ratio of the AUC determined after oral administration on the AUC determined after intravenous administration. Typically, an inhibitor having a low oral bioavailability has an oral bioavailability inferior or equal to 20%. Examples of inhibitors of factor Xa activity having a low oral bioavailability are well-known from the skilled person and include DX-9065, otamixaban, idraparinux, idrabiotaparinux and enoxaparin.

In another embodiment, the factor Xa inhibitor used in the context of the invention is an inhibitor of factor Xa expression.

As used herein, an "inhibitor of expression" refers to a natural or synthetic compound that has a biological effect to inhibit or significantly reduce the expression of a gene. Consequently an "inhibitor of factor Xa expression" refers to a natural or synthetic compound that has a biological effect to inhibit or significantly reduce the expression of the gene encoding for the factor X.

Inhibitors of factor Xa expression for use in the present invention may be based on anti-sense oligonucleotide constructs. Anti-sense oligonucleotides, including anti-sense RNA molecules and anti-sense DNA molecules, would act to directly block the translation of factor X mRNA by binding thereto and thus preventing protein translation or increasing mRNA degradation, thus decreasing the level of factor X, and accordingly of factor Xa, and thus activity, in a cell. For example, antisense oligonucleotides of at least about 15 bases and complementary to unique regions of the mRNA transcript sequence encoding factor X can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of factor Xa expression for use in the present invention. Factor Xa expression can be reduced by contacting a subject or cell with a small double stranded RNA (dsRNA), or a vector or construct causing the production of a small double stranded RNA, such that factor X expression is specifically inhibited (i.e. RNA interference or RNAi). Methods for selecting an appropriate dsRNA or dsRNA-encoding vector are well known in the art for genes whose sequence is known (e.g. see Tuschl et al. (1999) *Genes Dev.* 13:3191-3197; Elbashir et al. (2001) *Nature* 411:494-498; Hannon (2002) *Nature* 418:244-251; McManus et al. (2002) *Nat Rev Genet.* 3:737-747; Brummelkamp et al. (2002) *Science* 296:550-553; U.S. Pat. Nos. 6,573,099 and 6,506,559; and International Patent Publication Nos. WO 01/36646, WO 99/32619, and WO 01/68836).

In another embodiment, short hairpin RNA (shRNA) can also function as inhibitors of factor Xa expression for use in the present invention. A small hairpin RNA or short hairpin RNA (shRNA) is a sequence of RNA that makes a tight hairpin turn that can be used to silence target gene expression via RNA interference (RNAi). Expression of shRNA in cells is typically accomplished by delivery of plasmids or through viral or bacterial vectors. The promoter choice is essential to achieve robust shRNA expression. At first, polymerase III promoters such as U6 and H1 were used; however, these promoters lack spatial and temporal control. As such, there has been a shift to using polymerase II promoters to regulate expression of shRNA. shRNA is an advantageous mediator of RNAi in that it has a relatively low rate of degradation and turnover.

In another embodiment, microRNA (miRNA) can also function as inhibitors of factor Xa expression for use in the present invention. A microRNA (miRNA) is a sequence of RNA that can be used to silence target gene expression via RNA interference (RNAi). Expression of miRNA in cells is typically accomplished by delivery of plasmids or through viral or bacterial vectors. Micro RNAs (miRNAs) constitute non coding RNAs of 21 to 25 nucleotides, which controls genes expression at post-transcriptional level. miRNAs are synthesized from ARN polymerase II or ARN polymerase III in a premiRNA of 125 nucleotides. Pre-miRNAs are cleaved in the nucleus by the enzyme Drosha, giving rise to a precursor called imperfect duplex hairpin RNA (or miRNA-based hairpin RNA). These imperfect duplex hairpin RNAs are exported from the nucleus to the cytoplasm by exportin-5 protein, where it is cleaved by the enzyme DICER, giving rise to mature miRNAs. miRNAs combine with RISC complex which allows total or partial annealing with the homologous single-stranded target mRNA. Partial annealing with the mRNA leads to the repression of protein translation, whereas total annealing leads to cleavage of the single-stranded mRNA.

Ribozymes can also function as inhibitors of factor Xa expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of factor X mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC.

Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of factor Xa expression can be prepared by known methods.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing factor Xa, more particularly intestinal cells expressing factor Xa. Preferably, the vector transports the nucleic acid to cells with reduced degradation relative to the extent of degradation that would result in the absence of the vector. In general, the vectors useful in the invention include, but are not limited to, plasmids, phagemids, bacteria, probiotics, viruses, other vehicles derived from viral or bacterial sources that have been manipulated by the insertion or incorporation of the antisense oligonucleotide siRNA or ribozyme nucleic acid sequences.

Plasmid vectors have been extensively described in the art and are well known to those of skill in the art. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Accordingly, in particular embodiment, the factor Xa inhibitor is selected from the group consisting of antisense RNA or DNA molecules, small inhibitory RNAs (siRNAs), short hairpin RNA (shRNA), micro ARN (miRNA) and ribozymes.

Subject

By "subject" is meant herein denotes a mammal, such as a rodent, a feline, a canine, and a primate. Preferably, a subject according to the invention is a human.

Preferably, the subject treated in the context of the invention is subjected to a high fat diet.

As used herein, "high fat diet" or "western diet" means a dietary consumption which contains greater than 20% of its total calories from fat. In some embodiments, the dietary consumption contains greater than 30% of its total calories from fat. In other embodiments, the dietary consumption contains greater than 40% of its total calories from fat. "High fat diet" and "western diet" are used interchangeably herein.

As used herein, "subjected to a high fat diet" means subjects or patients which consume a high fat diet as described above.

Preferably, the subject treated in the context of the invention is a subject having or suspected of having or predisposed to diseases, disorders and/or conditions characterized in whole or in part by hyperglycemia, impaired glucose tolerance, impaired fasting glucose and/or insulin resistance. More preferably, the subject treated in the context of the invention is a subject suffering from hyperglycemia, impaired glucose tolerance, impaired fasting glucose, insulin resistance and/or diabetes.

In a preferred embodiment, the treated subject does not suffer from thrombosis and/or is not at risk of thrombosis.

Medical Indications

The present invention is drawn to a factor Xa inhibitor, as defined in the section "Factor Xa inhibitor" above for use as a medicament in a method for regulating, in particular decreasing, glycemia in a subject, as defined in the section "Subject" above.

The present invention also concerns a method for regulating, in particular decreasing, glycemia in a subject in need thereof, comprising administering to said subject a therapeutically effective amount of a factor Xa inhibitor, as defined in the section "Factor Xa inhibitor" above.

The present invention is also drawn to the use of a factor Xa inhibitor, as defined in the section "Factor Xa inhibitor" above in the manufacture of a medicament intended to regulate, in particular decrease, glycemia in a subject, as defined in the section "Subject" above.

By "glycemia regulation" or "regulating glycemia" is meant herein controlling the blood glucose level in a subject, so that this glucose level remains normal.

"Normal glucose levels" refers to glucose levels that are not considered abnormal. Normal glucose levels can include normal glucose tolerance and normal fasting glucose levels. "Normal glucose tolerance" refers to glucose levels that are below impaired glucose tolerance levels, i.e., a 2 hour post 75 g glucose load plasma glucose level that is lower than 7.8 mmol/l (140 mg/dl). "Normal fasting glucose" refers to a fasting plasma glucose level that is below impaired fasting glucose, i.e., less than 6.1 mmol/l (110 mg/dl).

The factor Xa inhibitor, as defined in the section "Factor Xa inhibitor" above is thus particularly useful for preventing and/or treating hyperglycemia, impaired glucose tolerance, impaired fasting glucose, insulin resistance and/or diabetes.

The present invention is thus also drawn to a factor Xa inhibitor, as defined in the section "Factor Xa inhibitor' above for use for preventing and/or treating hyperglycemia, impaired glucose tolerance, impaired fasting glucose, insulin resistance and/or diabetes.

The present invention also concerns a method for preventing and/or treating hyperglycemia, impaired glucose tolerance, impaired fasting glucose, insulin resistance and/or diabetes in a subject, comprising administering to said subject a therapeutically effective amount of a factor Xa inhibitor, as defined in the section "Factor Xa inhibitor" above.

The present invention is also drawn to the use of a factor Xa inhibitor, as defined in the section "Factor Xa inhibitor' above in the manufacture of a medicament intended for the prevention and/or the treatment of hyperglycemia, impaired glucose tolerance, impaired fasting glucose, insulin resistance and/or diabetes in a subject.

The term "hyperglycemia", as used herein, refers to any elevated level of blood glucose compared to a basal level in a subject. "Basal level", as used herein, refers to a blood glucose level of a normal subject when fasting. Generally, hyperglycemia refers to blood glucose levels above about 100 mg/dl. In particular, hyperglycemia refers to blood glucose levels above about 110 mg/dl when fasting and above about 140 mg/dl two hours after having a meal.

As used herein, "impaired glucose tolerance" (IGT) or "glucose intolerance" is defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75-g oral glucose tolerance test. These glucose levels are above normal but below the level that is diagnostic for diabetes.

As used herein, "impaired fasting glucose" refers to fasting serum glucose values greater than 110 mg/dL measured on at least two separate occasions.

As used herein, "insulin resistance" refers to a condition in which the cells of the body become resistant to the effects of insulin, that is, the normal response to a given amount of insulin is reduced. As a result, higher levels of insulin are needed in order for insulin to exert its effects.

The term "diabetes", as used herein, refers to any kind of diabetes associated with high blood glucose levels. It refers to a glucose level higher or equal 11.1 mmol/l (200 mg/dl) after a 2 hour oral glucose tolerance test and/or to a fasting plasma glucose higher or equal to 7.0 mmol/l (126 mg/dl). "Diabetes" comprises, e.g., type 1 diabetes, type 2 diabetes, steroid diabetes (Morbus Cushing), gestational diabetes and kinds of secondary diabetes induced by other disease states (e.g., pancreatitis, obesity). Preferably, diabetes is type 2 diabetes.

In its broadest meaning, the term "treating" or "treatment" refers to reversing, alleviating, inhibiting the progress of, the disorder or condition to which such term applies, or one or more symptoms of such disorder or condition.

The factor Xa inhibitor may be administered in the form of a pharmaceutical composition, as defined below.

Preferably, said inhibitor is administered in a therapeutically effective amount.

As used herein, the expression "therapeutically effective amount" means any amount of a drug which, when administered to a patient in need thereof, will achieve a beneficial pharmacological effect or therapeutic improvement consistent with the objectives of the present invention without causing serious, adverse or otherwise treatment-limiting side effects (at a reasonable benefit/risk ratio), within the scope of sound medical judgment.

The factor Xa inhibitor used in the context of the invention may be combined with pharmaceutically acceptable excipients, and optionally sustained-release matrices, such as biodegradable polymers, to form pharmaceutical compositions.

Preferably, the factor Xa inhibitor used in the context of the invention has a controlled intestinal release.

As used herein, the expression "controlled intestinal release" means the factor Xa inhibitor is administered under a formulation or dosage enabling the specific release and/or action of the active compound in the intestine only. In some embodiments, the controlled intestinal release is obtained by administration of the factor Xa inhibitor in an amount low enough to have intestinal effect only and no systemic effect. For example, concentrations of 0.2, 0.5 or 1 mg/kg are suitable for controlled intestinal release. Alternatively the controlled intestinal release can be obtained by the use of a factor Xa inhibitor that has poor systemic bioavailability.

The factor Xa inhibitors used in the context of the invention may be administered by any suitable route, in particular by oral, sublingual, parenteral (such as subcutaneous, intramuscular, intravenous or transdermal), local or rectal route. Preferably, the factor Xa inhibitors used in the context of the invention are administered orally.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms, liposomal formulations, time release capsules, and any other form currently used.

The factor Xa inhibitor used in the context of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

It will be understood that the total daily usage of the compounds of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 10 mg/kg per adult per day.

The factor Xa inhibitor used in the context of the invention can be used in combination with an anti-diabetic agent.

Anti-diabetic agents that can be used in these combination therapies include insulin; sulfonylurea compounds, such as glyburide, tolbutamide, acetohexamide, tolazamide, chlorpropamide, glipizide, glimepiride or gliclazide; meglitinides, such as repaglinide or nateglinide; biguanides, such as metformin, phenformin or buformin; thiazolidinediones, such as rosigliazone, pioglitozone or troglitazone, alpha-glucosidase inhibitors, such as miglitol or asarabose; peptides or peptide analogs, such as glucagon-like peptide 1, gastric inhibitory peptide, exenatide, exendin-4, liraglutide or taspoglatide; DPP-IV inhibitors, such as vildagliptin or sitaliptin; amylin analogs, such as pramlintide; PPARα/γligands, such as aleglitazar, muraglitazar or tesaglitazar; SGLT (sodium-dependent glucose transporter 1) or FBPase (fructose 1,6-bisphosphatase) inhibitors, such as those disclosed in U.S. Pat. Nos. 6,967,193 ; 6,965,033 ; 6,919,322 ; 6,849,476 ; 6,399,782 ; or 6,110,903.

These antidiabetic agents can be formulated in the same pharmaceutical composition as the one including the factor Xa inhibitor of the invention or can be formulated in a separate composition. Accordingly, the antidiabetic agents may be administered separately, simultaneously or sequentially, with the factor Xa inhibitors used in the context of the invention.

The present invention is further illustrated by the following figures and examples.

EXAMPLES

Example 1

Material and Methods

Mice

Eight week old C57BL/6 male mice were from Charles River laboratory. Mice were housed in individual cages under specific pathogen-free conditions, maintained in a temperature-controlled room with a 12 h light/dark cycle, and provided ad libitum access to water. Mice were fed with either a regular low fat diet or a high-fat diet (72% fat (corn oil, lard), 28% protein, <1% carbohydrate, Safe). This diet was demonstrated to generate fasting hyperglycemia, glucose intolerance and insulin resistance after one month of diet treatment (Burcelin et al. *AJPEM*, 2002, 282 (4):E834-842). For Rivaroxaban (ApexBio) treatments, mice were orally gavaged with saline, or with Rivaroxaban (1, 2.5 or 5 mg/kg/mouse, 6 days per week) for four weeks. Animal usage was in compliance with and approved by the local ethical committee of Toulouse.

Microarrays

Jejunum mucosa of NC, HFD and HFD +symbiotic (prebiotic polydextrose PDX 0.2 g/mouse/day and probiotic *Bifidobacterium animalis* ssp. *lactis* 420 $10^9$ bacteria/mouse/day (Dupont Nutrition & Health, Kantvik, Finland)) mice was collected and frozen in liquid nitrogen. Total RNA was extracted, amplified and genome-wide gene expression profiling was performed using Agilent whole mouse genome oligo microarray 8×60K by GeT-TRiX core facility (Genome et Transcriptome, INRA, Toulouse, France). Agilent Feature Extraction reports were analyzed in R/Bioconductor.

Metabolic Measures

An Oral Glucose Tolerance Test (OGTT) was performed on 6-hfasted mice. Mice were gavage with a glucose solution (1.5 g/kg glucose, 20% glucose solution). Glycemia was measured with a glucometer (Roche Diagnostics) from blood collected at the tail vein 30 min before the glucose injection and 15, 30, 60, 90 and 120 min after the gavage. The glucose tolerance index was calculated by adding the glycemic values from 30 to 90 min after glucose gavage divided by the corresponding duration.

Statistical Analysis

All values were expressed as means±SEM (standard error of the mean). Statistical analyses were conducted using GraphPad PRISM (version 6.03). Statistical significance was determined using one- or two-way ANOVA followed by the Tukey post-hoc test when appropriate. P-values less than 0.05 were considered to be statistically significant.

Results mRNA Expression of Factor X in Jejunum Increases after 4 weeks of High Fat Diet (HFD) and Decreases with Symbiotic Treatment.

Figure 1:
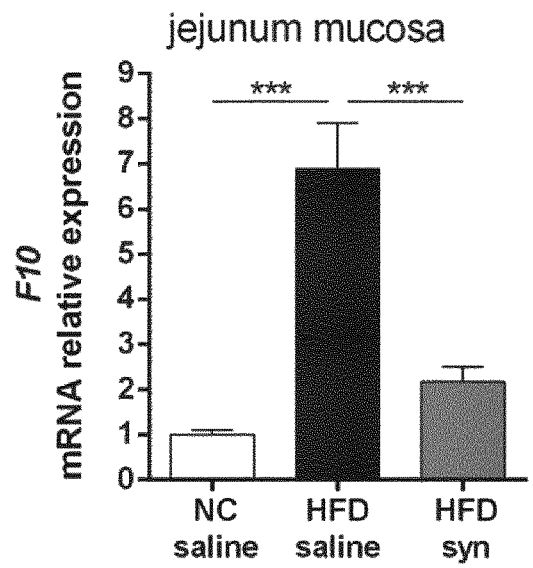
FIG. 1: mRNA expression of Factor X (F10) in jejunum mucosa after 4 weeks of High Fat Diet. F10 Microarray analysis of coagulation factor X mRNA expression in the jejunum mucosa of adult normal chow (NC saline), high fat diet (HFD saline) or HFD mice treated with symbiotic (HFD syn) for four weeks (n=6 per group). Data were analyzed by one-way ANOVA with Tukey's multiple comparison tests and presented as mean±S.E.M. ***P<0.001.

The mRNA expression of coagulation factor X significantly increased (7-fold) after four weeks of HFD in the jejunum mucosa compared to normal chow diet. Interestingly when HFD mice were treated daily with a mix of pre- and probiotic, Factor X mRNA expression was not different compared to normal chow mice, suggesting a regulation of this gene by gut microbiota (FIG. 1).

Chronic Treatment with Rivaroxaban Increases Glucose Tolerance after 4 weeks of High Fat Diet.

In order to determine if the increase of Factor X mRNA expression in HFD mice leads to diabetes development, the inventors treated HFD mice with a well know Factor Xa inhibitor (Rivaroxaban).

Figure 2:
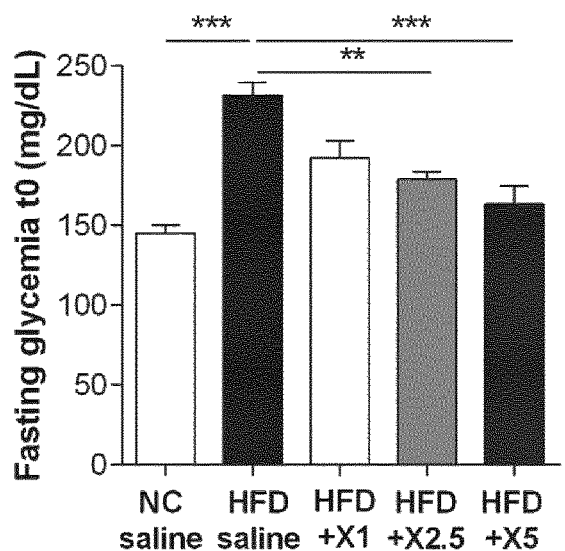
FIG. 2: NC or HFD C57/BL6 mice were gavaged daily with saline or one of three doses of Rivaroxaban (1, 2.5 or 5; n=5 per group) for 4 weeks. Histograms show fasting glycemia after 4 weeks of chronic treatment with Rivaroxaban. NC saline: control C57/BL6 mice fed with normal chow and gavaged with saline for 4 weeks. HFD saline: control C57/BL6 mice fed with high fat diet and gavaged with saline for 4 weeks. HFD+X1: C57/BL6 mice fed with high fat diet and gavaged with 1 mg/kg Rivaroxaban for 4 weeks. HFD+X2.5: C57/BL6 mice fed with high fat diet and gavaged with 2.5 mg/kg Rivaroxaban for 4 weeks. HFD+X5: C57/BL6 mice fed with high fat diet and gavaged with 5 mg/kg Rivaroxaban for 4 weeks. Data were analyzed by either one or two-way ANOVA with Tukey's multiple comparison tests and presented as mean±S.E.M. *P<0.05, P<0.01, *P<0.001.

A 72% high fat-enriched diet increased significantly fasting glycemia 1.5 fold when compared with normal chow (NC) mice. Interestingly, this increase was abolished in mice treated with different doses of Rivaroxaban (FIG. 2).

Figure 3:
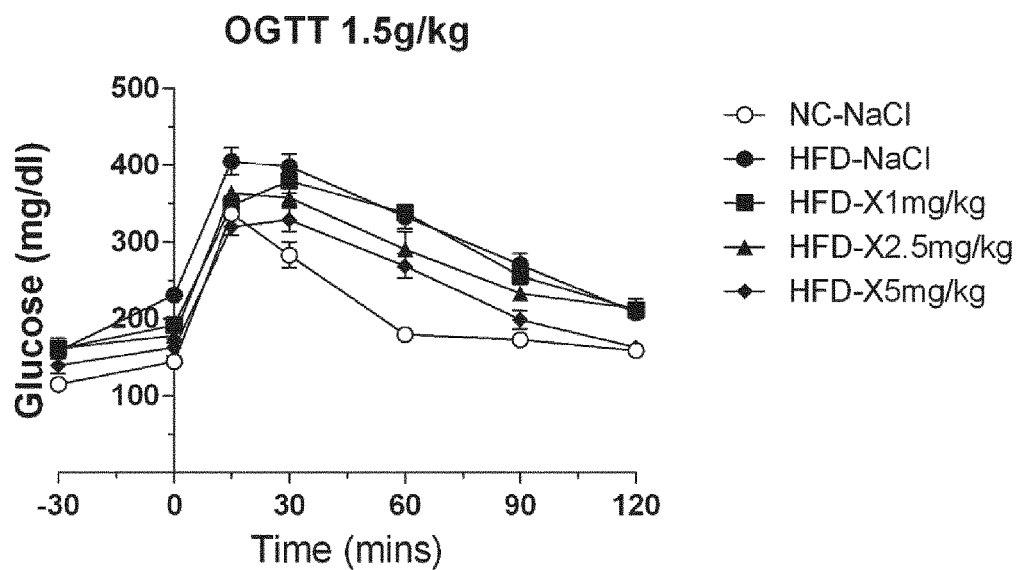
FIG. 3: NC or HFD C57/BL6 mice were gavaged daily with saline or one of three doses of Rivaroxaban (1, 2.5 or 5; n=5 per group) for 4 weeks. Graphs show oral glucose tolerance test (OGTT) (1.5 g/kg) after 4 weeks of chronic treatment with Rivaroxaban. NC-NaCl: control C57/BL6 mice fed with normal chow and gavaged with saline for 4 weeks. HFD-NaCl: control C57/BL6 mice fed with high fat diet and gavaged with saline for 4 weeks. HFD-X1 mg/kg: C57/BL6 mice fed with high fat diet and gavaged with 1 mg/kg Rivaroxaban for 4 weeks. HFD-X2.5 mg/kg: C57/BL6 mice fed with high fat diet and gavaged with 2.5 mg/kg Rivaroxaban for 4 weeks. HFD-X5 mg/kg: C57/BL6 mice fed with high fat diet and gavaged with 5 mg/kg Rivaroxaban for 4 weeks.

Similarly, following oral glucose challenge, blood glucose concentration was higher in HFD mice compared to NC mice. However, when HFD mice were treated (oral) with Rivaroxaban 1, 2.5 or 5 mg/kg, blood glucose concentration was reduced compared to HFD mice gavaged with saline (FIG. 3).

Figure 4:
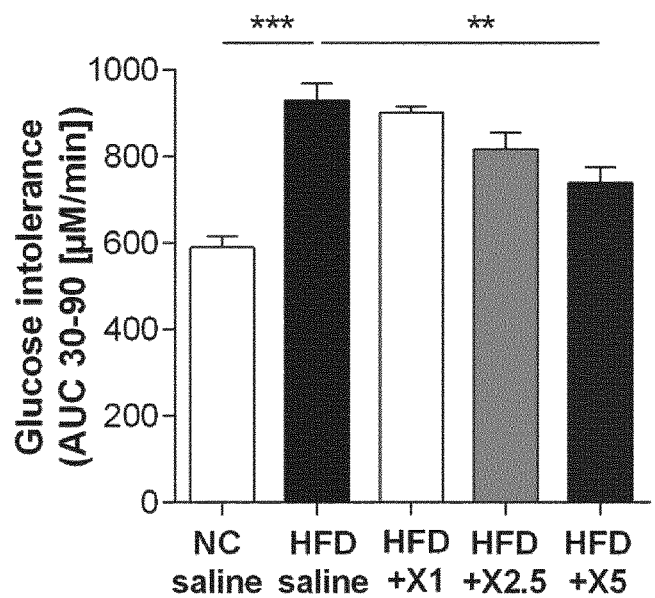
FIG. 4: NC or HFD C57/BL6 mice were gavaged daily with saline or one of four doses of Rivaroxaban (1, 2.5 or 5; n=5 per group) for 4 weeks. Histograms show glucose intolerance corresponding index (μM/min) from 30 min to 90 min after glucose administration. NC saline: control C57/BL6 mice fed with normal chow and gavaged with saline for 4 weeks. HFD saline: control C57/BL6 mice fed with high fat diet and gavaged with saline for 4 weeks. HFD+X1: C57/BL6 mice fed with high fat diet and gavaged with 1 mg/kg Rivaroxaban for 4 weeks. HFD+X2.5: C57/BL6 mice fed with high fat diet and gavaged with 2.5 mg/kg Rivaroxaban for 4 weeks. HFD+X5: C57/BL6 mice fed with high fat diet and gavaged with 5 mg/kg Rivaroxaban for 4 weeks. Data were analyzed by either one or two-way ANOVA with Tukey's multiple comparison tests and presented as mean±S.E.M. *P<0.05, P<0.01, *P<0.001.

The glucose intolerance index increased significantly 1.7 times in HFD mice compared with normal chow mice. This increase was reduced in HFD mice treated with 5 mg/kg of Rivaroxaban (FIG. 4).

Figure 5:
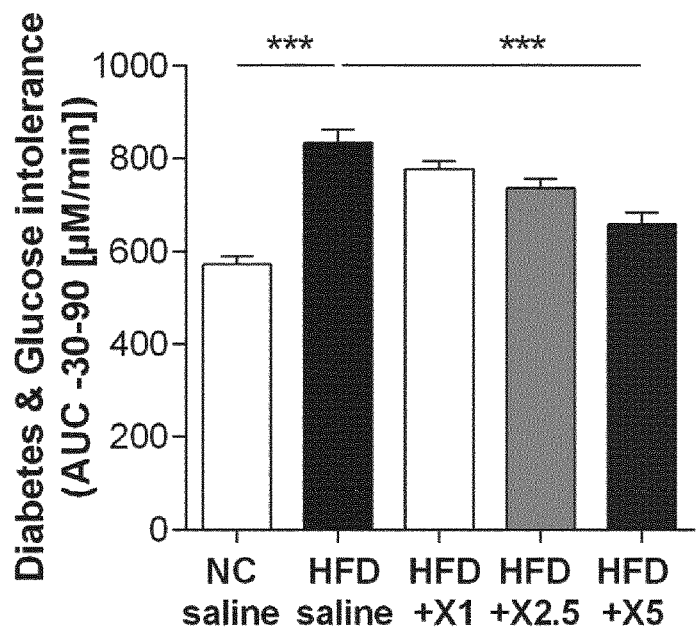
FIG. 5: NC or HFD C57/BL6 mice were gavaged daily with saline or one of four doses of Rivaroxaban (1, 2.5 or 5; n=5 per group) for 4 weeks. Histograms show diabetes and glucose intolerance corresponding index (µM/min) from 30 min before to 90 min after glucose administration. NC saline: control C57/BL6 mice fed with normal chow and gavaged with saline for 4 weeks. HFD saline: control C57/BL6 mice fed with high fat diet and gavaged with saline for 4 weeks. HFD+X1: C57/BL6 mice fed with high fat diet and gavaged with 1 mg/kg Rivaroxaban for 4 weeks. HFD+X2.5: C57/BL6 mice fed with high fat diet and gavaged with 2.5 mg/kg Rivaroxaban for 4 weeks. HFD+X5: C57/BL6 mice fed with high fat diet and gavaged with 5 mg/kg Rivaroxaban for 4 weeks. Data were analyzed by either one or two-way ANOVA with Tukey's multiple comparison tests and presented as mean±S.E.M. *P<0.05, P<0.01, *P<0.001.

The diabetes and glucose intolerance index increased significantly 1.5 times in HFD mice compared with normal chow mice. HFD mice treated with 5 mg/kg of Rivaroxaban showed a significant reduction of this index compared to HFD saline mice (FIG. 5).

These data thus demonstrate a role of coagulation factor X in the regulation of glycemia, and the interest of factor Xa inhibitors for regulating glycemia, in particular in patients subjected to high fat diet.

Example 2

Inhibition of Intestinal FXa Decreases Bacterial Translocation

Figure 6:
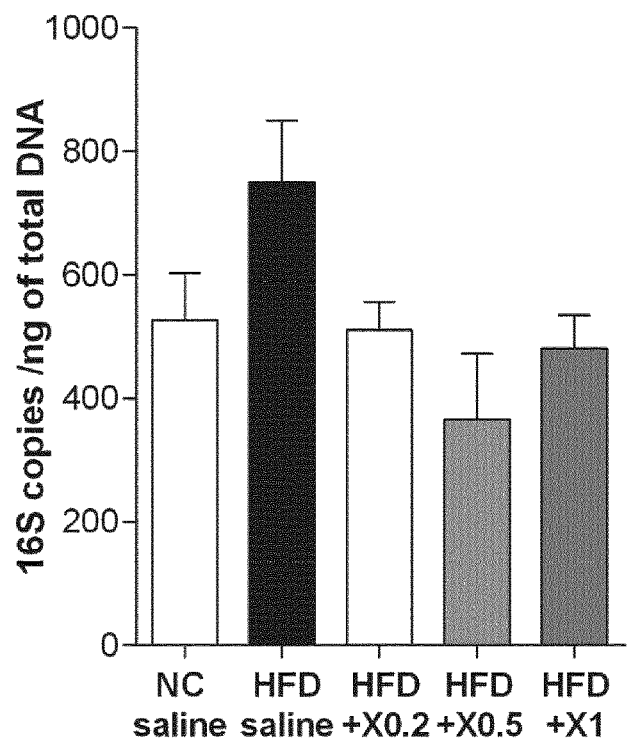
FIG. 6: Bacterial translocation in mesenteric adipose tissue of HFD mice treated or not with an oral anti FXa

To explore whether intestinal FXa inhibition regulates intestinal permeability the inventors have treated HFD mice daily during 4 weeks with 3 different doses of Rivaroxaban by oral gavage. The inventors chose low Rivaroxaban concentrations (0.2, 0.5 and 1 mg/kg) to have an intestinal effect only and avoid systemic anti-coagulation. After 4 weeks of treatment the number of 16S rDNA copies was measured in mesenteric adipose tissue in order to evaluate bacterial translocation. These results indicate that low doses of Rivaroxaban are able to reduce bacterial translocation in HFD mice compared to non-treated HFD mice (FIG. 6) suggesting a decrease of gut permeability with Rivaroxaban.

Example 3

Figure 7:
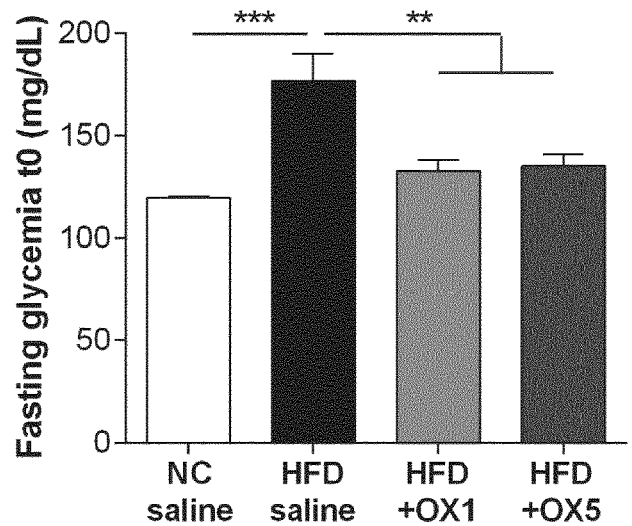
FIG. 7: Fasting glycaemia of HFD mice treated or not with oral Otamixaban
Figure 8:
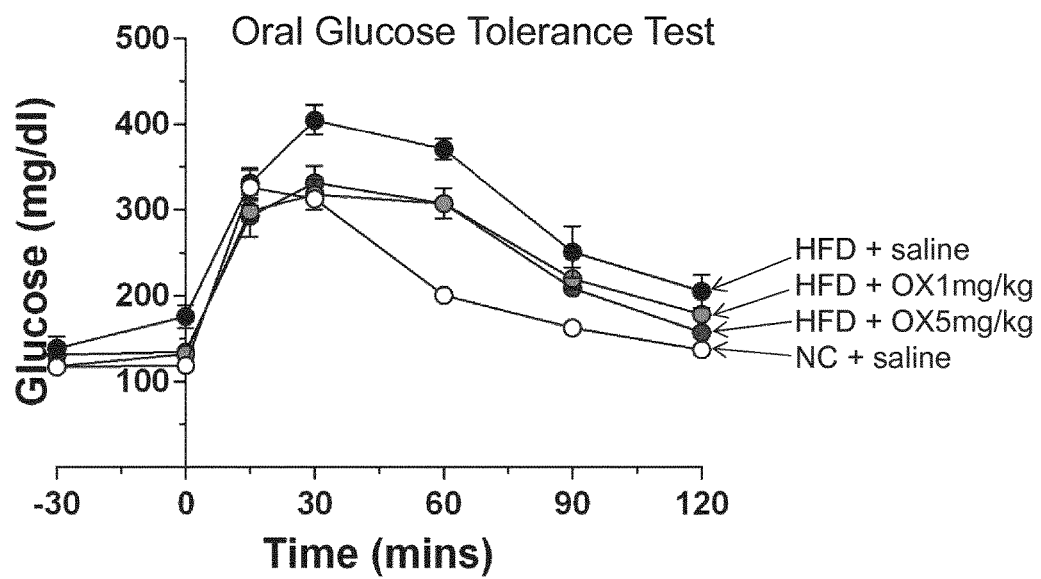
FIG. 8: Oral glucose tolerance test (OGTT) of HFD mice treated or not with oral Otamixaban

Inhibition of Intestinal Factor Xa using Otamixaban Reduces Fasting Glycemia and Glucose Intolerance in HFD Mice Further to the demonstration that rivaroxiban impacts on the parameters of type 2 diabetes, the inventors treated mice with two different doses of Otamixaban (1 and 5 mg/kg) by oral gavage. The inventors chose Otamixaban because of its low bioavailability which will result in a selective intestinal effect. After 4 weeks of treatment the inventors measured fasting glycaemia and glucose intolerance (FIGS. 7 and 8). The results show that oral Otamixaban reduces fasting glycaemia after 4 weeks of treatment (FIG. 7) and reduces glucose intolerance (FIG. 8) suggesting that the inhibition of FXa specifically in the intestine is able to control glycaemia and reduce glucose intolerance associated with HFD.

These data indicate that intestinal factor Xa regulates permeability and bacterial translocation which can mediate glucose intolerance.

The invention claimed is:

1. A method for regulating glycemia in a subject in need thereof, comprising administering to said subject a therapeutically effective amount of a factor Xa inhibitor, wherein said factor Xa inhibitor is a direct inhibitor of factor Xa activity and/or an inhibitor of factor Xa expression.

2. The method according to claim 1, wherein said factor Xa inhibitor is selected from the group consisting of rivaroxaban, otamixaban, darexaban, LY517717 and eribaxaban.

3. The method according to claim 1, wherein said factor Xa inhibitor is selected from the group consisting of rivaroxaban and otamixaban.

4. The method according to claim 1, wherein said factor Xa inhibitor is an inhibitor of factor Xa expression.

5. The method according to claim 4, wherein said factor Xa inhibitor is selected from the group consisting of antisense RNA or DNA molecules, small inhibitory RNAs (siRNAs), short hairpin RNA and ribozymes.

6. The method according to claim 1, wherein the subject is subjected to a high fat diet.

7. The method according to claim 1, for preventing and/or treating hyperglycemia, impaired glucose tolerance, impaired fasting glucose, insulin resistance and/or diabetes.

8. The method according to claim 7, wherein diabetes is type 2 diabetes.

9. The method according to claim 7, wherein said factor Xa inhibitor is used in combination with an anti-diabetic agent.

10. The method according to claim 1, wherein said factor Xa inhibitor has a controlled intestinal release.

* * * * *